United States Patent [19]

Andrews

[11] Patent Number: 4,476,312
[45] Date of Patent: Oct. 9, 1984

[54] PROCESSES FOR MAKING 3-METHYLTHIOPHENE-2-CARBOXALDEHYDE AND INTERMEDIATES THEREFOR

[75] Inventor: Glenn C. Andrews, Waterford, Conn.

[73] Assignee: Pfizer Inc., New York, N.Y.

[21] Appl. No.: 581,463

[22] Filed: Feb. 17, 1984

Related U.S. Application Data

[62] Division of Ser. No. 381,596, May 24, 1982.

[51] Int. Cl.$^3$ .................... C07D 333/24; A61K 31/38
[52] U.S. Cl. ........................................ 549/70; 424/275
[58] Field of Search ........................................... 549/70

[56] References Cited

U.S. PATENT DOCUMENTS 2,601,479  6/1952  Weston ................................. 549/70
2,853,493  9/1958  Weston ................................. 549/70

FOREIGN PATENT DOCUMENTS 58-49378  3/1983  Japan ..................................... 549/70

Primary Examiner—Alan Siegel
Attorney, Agent, or Firm—Charles J. Knuth; A. E. Frost; Mark Dryer

[57] ABSTRACT

Processes for preparing isometrically pure 3-methylthiophene-2-carboxaldehyde, an intermediate for synthesis of anthelmintic agents, by reaction of mercaptoacetaldehyde or the dimer, or a polymer thereof, or a dialkylacetal thereof in the presence of a base with (1) methyl vinyl ketone or an alpha- or beta- oxidized derivative of methyl vinyl ketone to form a 3-oxobutylmercaptoacetaldehyde or dialkyl acetal thereof, or an alpha- or beta-substituted derivative thereof which is then converted to 3-methylthiophene-2-carboxaldehyde via appropriate steps including, if necessary, treatment with acid, followed, if necessary, by enamine catalyzed cyclization and, in the case of using methyl vinyl ketone as reactant, a dehydrogenation step; or (2) 3-butyn-2-one to produce a mixture of isomeric 3-oxobut-1-enylmercaptoacetaldehyde or dialkyl acetals thereof which is cyclized to 3-methylthiophene-2-carboxaldehyde.

A further aspect of this invention is an improved process for making dialkyl acetals of 2-mercaptoacetaldehyde which comprises reacting an alkyl vinyl ether with sulfur chloride to produce a bis(2-chloro-2-alkoxyethyl)disulfide which is then treated with an alcohol to afford a bis(2,2-dialkoxyethyl)disulfide which is reduced under alkaline conditions to 2-mercaptoethyl acetaldehyde alkali metal salt which can be alkylated to a thioether, a valuable intermediate.

1 Claim, No Drawings

PROCESSES FOR MAKING 3-METHYLTHIOPHENE-2-CARBOXALDEHYDE AND INTERMEDIATES THEREFOR

This is a division of application Ser. No. 381,596, filed May 24, 1982.

BACKGROUND OF THE INVENTION

This invention relates to processes for making 3-methylthiophene-2-carboxaldehyde which comprise Michael reaction of a dialkyl acetal of 2-mercaptoacetaldehyde or 2-mercaptoacetaldehyde itself or its equivalent with (1) methyl vinyl ketone or an alpha- or beta-oxidized derivative of methyl vinyl ketone to form a 3-oxobutylmercaptoacetaldehyde or a dialkyl acetal thereof which is then converted to 3-methylthiophene-2-carboxaldehyde via appropriate steps including treatment with acid, followed, if necessary, by enamine catalyzed cyclization and, in the case of using methyl vinyl ketone as reactant, a dehydrogenation step; or (2) 3-butyne-2-one to produce a mixture of isomeric 3-oxobut-1-enylmercaptoacetaldehyde or dialkyl acetals thereof which is cyclized to 3-methylthiophene-2-carboxaldehyde, an intermediate for the syntheses of anthelmintic agents.

A further aspect of this invention is an improved, one-pot process for making dialkyl acetals of 2-mercaptoacetaldehyde, useful as intermediates for a variety of valuable products including various thioethers and 3-methylthiophene-2-carboxaldehyde.

Prior art methods for making 3-methylthiophene-2-carboxaldehyde produce a mixture of said compound and the isomeric 4-methylthiohene-2-carboxaldehyde and/or poor yields of the desired 3-isomer. The production of isomeric mixtures necessitates, for many purposes, a separation of said isomers. This, of course, results in reduced yield of the desired 3-methyl isomer and an increase in cost thereof.

Direct formylation of 3-methylthiophene using (1) formaldehyde and ammonium chloride is reported by Hartough, "Thiophene and Its Derivatives", Interscience Publishers Inc., 1952, p. 510, to give an 11% yield of formylation product in which the ratio of 3- to 4-methylthiophene-2-carboxaldehyde was 99:1; (2) N,N-dimethylformamide and phosphorous oxychloride is reported by Campaigne et al., J. Am. Chem. Soc. 75, 989–991 (1953) to afford a 41% yield of formylation product in which the ratio of 3-isomer to 4-isomer was 78:22.

Still further, King et al., J. Org. Chem., 13, 635 (1948) describe production of an 85% yield of formylation product comprising a 78:22 ratio of 3- to 4-methyl thiophene-2-carboxaldehyde by direct formylation of 3-methylthiophene using phosphorous oxychloride and N-methylformanilide. Direct formylation processes are also described in U.S. Pat. No. 2,853,493, issued Sept. 23, 1958. Gronowitz et al., Arkiv. Kemie 17, 165–77 (1961) describe preparation of 3-methylthiophene-2-carboxaldehyde by reaction of 3-methyl-2-thienyl magnesium bromide with N,N-dimethylformamide. British Pat. No. 1,176,312 published Jan. 1, 1970 describes preparation of 3-methylthiophene-2-carboxaldehyde containing a small proportion of its 4-isomer by reaction of 3-methylthiophene and dichloromethyl methyl ether in the presence of a Friedel-Crafts catalyst.

Tilak et al., Tetrahedron Letters No. 24, 1609–1612 (1964) report a general method for preparation of 2-carboethoxythiophenes which comprises condensation of ethyl mercaptoacetate with an alpha,beta-unsaturated ketone to form a 2-carboethoxy-3-hydroxy-3-methyltetrahydrothiophene which is then dehydrated to a dihydrothiophene using polyphosphoric acid. Dehydrogenation of said dihydrothiophene by means of diphenyl disulfide or chloranil produces the corresponding 2-carboethoxy-3-methylthiophene. Hydrolysis and decarboxylation afford a 3-methylthiophene.

Preparation of 2-methyl-5-isopropenyl-1-cyclopentene-1-carboxaldehyde by an enamine directed aldol condensation is reported by Wolinsky et al. in J. Org. Chem. 29, 3740–3742 (1964).

The use of activated manganese dioxide as a dehydrogenating agent is reviewed by Fatiadi in Synthesis, March 1976, pages 133–136. Minster et al., J. Org. Chem. 43, 1624–6 (1978) and 44, 497–501 (1979) report on the use of nickel peroxide as oxidant for partially reduced heterocycle compounds.

Parham et al., J. Am. Chem. Soc., 75, 2065–2069 (1953) report the preparation of dimethyl mercaptoacetal. Japanese Pat. No. 5328, published July 30, 1955, describes the preparation of bis(2-alkoxyethyl)disulfides by reaction of vinyl alkyl ethers with monochlorosulfide.

Several processes for making 2-mercaptoacetaldehyde dimethylacetal (I, $R_1=R_2=CH_3$) are reported by Parham et al., J. Am. Chem. Soc. 75, 2065–2069 (1953). These processes involve reaction of 2-chloroacetaldehyde dimethyl acetal with (1) benzylmercaptan sodium salt to produce benzyl-(1,1-dimethoxy ethyl)sulfide which was then reduced with sodium/ammonia to the desired acetal; (2) sodium sulfide to form 1,1,1',1'-tetramethoxyethyl disulfide followed by reduction of said disulfide using sodium/ammonia or lithium aluminum hydride; and (3) sodium polysulfide to give a mixture of polysulfides which was reduced with sodium/ammonia. A fourth process described in said reference comprises the action of potassium hydrosulfide on diethyl or dimethyl bromoacetal to produce the corresponding dialkyl mercaptoacetal.

The reaction of mercaptoacetaldehyde and 1,4-dithian-2,5-diol, its dimer, with nitriles such as cyanoacetic acid to produce 2-aminothiophene derivatives are described by Gewald, Angew. Chem. 73, 114 (1961) and Robba, et al., Bull Soc. Chim. Fr. 12, Pt. 2, 2864–70 (1974), respectively. German Offenlegungsschrift No. 2,808,321 (C.A. 90, 7591k, 1979) reports the reaction of 1,4-naphthoquinone with the dimer to produce 2-[(formylmethyl)thio]-1,4-naphthoquinone which was cyclized in sulfuric acid to 4,9-dihydronaphtho[2,3-b]thiophen-4,9-dione. Hesse et al., Chem. Ber. 85, 924–32 (1952) report that in solution an equilibrium exits between mercaptoacetaldehyde and its dimer.

The processes of this invention, in contrast to the prior art methods for making 3-methylthiophene-2-carboxaldehyde, afford the isomerically pure product by procedures which are easily carried out and which afford satisfactory yields of product.

SUMMARY OF THE INVENTION

It has now been found that isomerically pure 3-methylthiophene-2-carboxaldehyde can be prepared by the reactions presented below wherein variables $R_1$ and $R_2$ when taken individually are ($C_{1-4}$) alkyl; or $R_1$ and $R_2$ when taken together are ($C_{2-3}$)alkylene, e.g., ethylene and propylene; X is ($C_{1-4}$)alkoxy; Y is hydrogen, ($C_{2-4}$)-alkanoyloxy; and $Y^0$ is Y or hydroxy.

Variables $R_1$ and $R_2$ can be alike or different. However, from a practical and economical standpoint $R_1$ and $R_2$ are the same when taken individually. Preferred values of $R_1$ and $R_2$ when so taken are methyl and ethyl. Also preferred are the cyclic acetals; i.e., those reactants (I) wherein $R_1$ and $R_2$ when taken together are $(C_{2-3})$alkylene.

The processes can be summarized as comprising reaction of a mercaptoacetaldehyde dialkyl acetal or mercaptoacetaldehyde generally in the presence of a base with: Route A—methyl vinyl ketone to produce a Michael adduct, a 3-oxobutylmercaptoacetaldehyde, or dialkyl acetal thereof, which is hydrolyzed to the aldehyde under acid conditions, and the aldehyde cyclized via enamine catalysis to 3-methyldihydrothiophene-2-carboxaldehyde and then dehydrogenated to 3-methylthiophene-2-carboxaldehyde (MTA); Route B—an alpha-oxidized derivative of methyl vinyl ketone to give a 2-substituted-3-oxobutylmercaptoacetaldehyde or a dialkyl acetal thereof which is treated with acid to give MTA; Route C—3-butyn-2-one to afford an epimeric mixture of 3-oxobut-1-enylmercapto acetaldehyde, or a dialkyl acetal thereof, which is cyclized to MTA; or Route D—a beta-oxidized derivative of methyl vinyl ketone to give the corresponding Michael adduct which is hydrolyzed and the resulting keto aldehyde cyclized via enamine catalysis to MTA.

In Route B, the Michael adduct of formula VI wherein $Y^0$ is hydroxy is produced from a compound of formula VI wherein $Y^0$ is alkanoyloxy by hydrolysis (e.g. $K_2CO_3$/methanol, not shown in the flow chart).

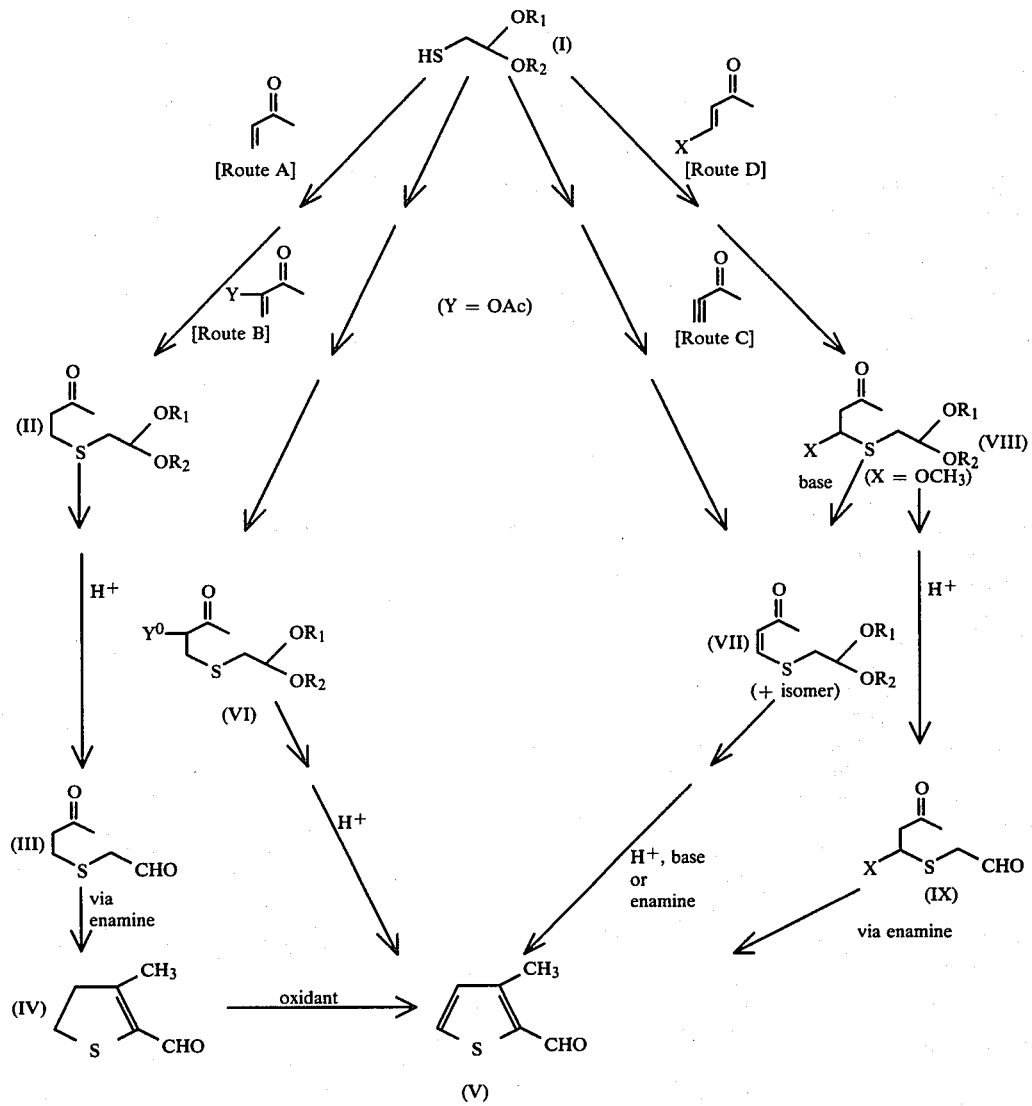

DETAILED DESCRIPTION OF THE INVENTION

The first step of each of the routes outlined above comprises Michael addition of a di[$(C_{1-4})$alkyl]-acetal of 2-mercaptoacetaldehyde (I) to methyl vinyl ketone (Route A), to an oxidized derivative of methyl vinyl ketone (Routes B and D) or to 3-butyn-2-one (Route C) in a reaction-inert solvent in the presence of a base. Alternatively, a preformed alkali metal salt of a formula (I) compound, said salt produced by methods described herein, can be used. Suitable reaction-inert solvents; i.e., solvents which do not react to an appreciable extent with reactants or products, are water, $(C_{1-4})$alcohols, aromatic hydrocarbons such as benzene, toluene, xylene, cyclohexane, hexane, ethers such as tetrahydrofuran, dioxane, mono and dimethyl ethers of ethylene glycol, and mixtures thereof.

Representative bases are relatively weak bases such as tetramethylammonium hydroxide, alkali metal hydroxides, alkali metal carbonates, tertiary amines such as triethylamine, pyridine, piperidine, N,N-dimethyl aniline and N-methylmorpholine. The choice of base is determined, in part, by the solvent used. When water or aqueous solvent systems are used, alkali metal carbonates are favored. When a non-aqueous solvent system is used, a tertiary amine is generally favored. Alcoholic solvents allow the use of alkali metal hydroxides since such bases are soluble in said solvents.

The amount of base used is not critical as regards any of Routes A, B, C or D. Amounts of base ranging from about 0.001 mole per mole of acetal reactant (I), to about equimolar amounts of each can be used. Preferred amounts of base, referred to herein as "catalytic" amounts of base, range from about 0.001 mole to about 0.10 mole per mole of acetal reactant.

In each of Routes A, B, C and D, the first step is carried out at temperatures ranging from 0° C. to the reflux temperature of the solvent system used. For convenience and ease of operation, ambient temperature is generally favored. The reaction time is, of course, somewhat dependent upon the temperature of the reaction. At ambient temperature, reaction times of from three to five hours are sufficient to achieve substantially complete reaction. At lower temperatures, e.g., 0° to 15° C., reaction periods of from five to twenty hours are generally required, while higher temperatures, e.g. 30° to reflux temperature of the solvent, generally require from two to four hours time.

In Route A, conversion of formula II compounds to formula III compounds is accomplished by hydrolysis with aqueous acids such as mineral acids, HCl H$_2$SO$_4$, HBr, and organic acids such as trifluoroacetic acid, trichloroacetic acid. A water miscible organic solvent can be used as cosolvent in this conversion, if desired. Representative of such solvents are acetone, tetrahydrofuran, dioxane, isopropanol.

This hydrolytic conversion is conducted at a temperature of from about 0° C. to 60° C. The reaction period depends, of course, upon the temperature of the reaction and upon the concentration of acid used.

Despite its important effect upon the time required for the hydrolysis, the concentration of aqueous acid used is not critical. The more concentrated the acid, the shorter the reaction time required. At acid concentrations of one molar, and at the upper part of the temperature range cited above, a reaction period of about ten minutes is sufficient to achieve complete hydrolysis. Under similar conditions, the use of 0.1 molar acid requires about four hours for complete hydrolysis. Concentrations of acid greater than one molar can be used but afford no advantage.

The keto-aldehyde hydrolysis product may be isolated from the hydrolysis reaction mixture or enamine catalyzed cyclization carried out in th aqueous solution at pH 4-7 using secondary amine catalysis.

The keto-aldehyde hydrolysis product (II) is, if desired, isolated from the reaction mixture by extraction with a water immiscible solvent such as ethyl acetate, methylene chloride, chloroform, benzene or toluene. Removal of the solvent gives the keto-aldehyde (III) as an oil.

However, the keto-aldehyde need not be recovered from the extract. In most instances it is more convenient and economical to use the keto-aldehyde containing extract directly in the cyclization step. Cyclization to the dihydrothiophene aldehyde (IV) is accomplished by enamine catalysis in a reaction-inert solvent. Reaction-inert solvents for the cyclization reaction include those enumerated above as extractants for III, and tetrahydrofuran, dioxane, 1,1,1-trichloroethane, water and mixtures thereof.

By-product water can be effectively removed from the reaction mixture by use of a solvent or solvents which form an azeotrope with the water thus permitting its removal by distillation. When a reaction-inert solvent is used which forms an azeotrope with water the reaction is conducted at the boiling point of the azeotropic mixture. In general, the temperature of the reaction can range from about 25° C. to about 150° C. Higher temperatures can, of course, be used particularly if a solvent which forms a higher boiling azeotrope is used. At temperatures below 25° C. the reaction is slow.

Further, drying agents such as magnesium sulfate, magnesium oxide and aluminum oxide also serve to effectively remove by-product water.

In addition to the solvents enumerated above, acetone, decalin and tetralin can be used especially when using molecular sieves for removal of water.

If aqueous solvents are used at pH 4-7, with amine catalysis, extraction, of the resulting dihydrothiophene from the aqueous layer is easily accomplished by any of the water immiscible solvents mentioned above.

Enamine catalysis is achieved through the agency of a secondary amine such as pyrrolidine, morpholine, piperidine, dimethylamine, diisopropylamine; secondary amine anion exchange resins such as a polystyrene resin having secondary amine functional groups, representative of which is Amberlite IRA-45 (available from Rohm & Haas Co.). The reaction is catalyzed by acids which have a pK value of 2–6. Representative of such acids are lower alkanoic acids and substituted lower alkanoic acids, suvch as acetic, propionic, and trifluoroacetic acids.

The mole ratio of ketoaldehyde:secondary amine is not critical but can vary widely from about 1:1 to 1:0.01. When an acid catalyst is used the mole ratio of acid to secondary amine can vary from about 1:1 to 0.5:1.

The 3-methyldihydrothiophene-2-carboxaldehyde (IV) is isolated from the reaction mixture, if desired, by known methods, such as washing the reaction mixture with water to remove the catalyst and evaporation of the solvent from the reaction mixture. The dihydrothiophene aldehyde (IV) is then oxidized to (V). Alternatively, and preferably, the oxidizing agent is added directly to the reaction mixture containing (IV).

Suitable oxidizing agents are N-bromoacetamide, N-bromosuccinimide, nickel perioxide, manganese dioxide, chloranil, 2,3-dichloro-5,6-dicyanobenzoquinone, disulfides and sulfur. In general from about 1–8 equivalents of oxidizing agent are used. From a practical standpoint about one equivalent of oxidizing agent is favored. However, in the case of nickel peroxide and manganese dioxide 4–8 equivalents are necessary for complete reaction. Manganese dioxide is a specially favored oxidizing agent because of its ease of removal from the reaction mixture and the satisfactory conversions it affords.

This oxidation reaction is carried out at temperatures ranging from ambient temperature to 215° C. for periods of from about 2–10 hours. Temperatures of from about 40° C. to about 100° C. are favored since a balance between reaction times, yields and energy consumption is realized.

Representative solvents for the oxidation are acetone, dioxane, tetrahydrofuran, benzene, toluene, and chlorinated hydrocarbons such as chloroform and methylene chloride.

In Route B, the Michael adduct (VI) is converted to (V) by treatment with aqueous acid at temperatures from about 40° C. to 110° C. The intermediate aldehyde corresponding to (VI) is not isolated, although it can be if desired, but is converted to (V) in a one-pot reaction. A co-solvent (acetone, isopropanol, dioxane and other water miscible solvents) can be added to the reaction mixture if needed to obtain and maintain a one-phase reaction. Suitable acids are mineral acids such as hydrochloric, hydrobromic, and sulfuric acids and trifluoroacetic acid. This route represents a favored route since the presence of a $Y^0$-substituent (acetoxy or hydroxy) directs cyclization resulting in exclusive formation of the desired isomers.

In Route D, the Michael adduct (VIII) is subjected to hydrolysis under conditions which hydrolyze only the dialkyl ketal moiety. Suitable conditions comprise the use of a strong mineral acid such as hydrochloric, hydrobromic or sulfuric acids, in aqueous media generally in the presence of a co-solvent such as acetone or other water miscible reaction-inert solvent. Alternatively, a strong mineral acid or organic acid such as trifluoroacetic, trichloroacetic acids in aqueous solution can be used. The hydrolysis is conducted at from about 0° to 25° C. for periods of up to two hours. Following completion of the hydrolysis, the ketoaldehyde (IX) is isolated by known procedures and said keto-aldehyde cyclized by enamine catalysis substantially according to the procedure described with respect to Route A. The temperature range for cyclization of (IX) to (V) is desirably from 40°–100° C. and, for best results, at about 60° C.

A variation of Route D when X is alkoxy, e.g., methoxy, involves base elimination of X from (VIII) to give an isomeric mixture of enone olefins (VII).

Isomeric compounds represented by (VII) are also obtained by Route C which comprises addition of 3-butyne-2-one to (I) in a $(C_{1-4})$alcohol medium in the presence of a base such as sodium or potassium carbonate at temperatures from about 30° C. to ambient temperature. The isomers are separable by chromatography on silica gel.

Treatment of the isomeric mixture or the individual isomers with a strong aqueous acid, e.g. HCl, trifluoroacetic acid, produces the isomeric mixture of 3-oxo-1-butenylmercaptoacetaldehydes, or the individual isomers, corresponding to formula (VII). Cyclization of said 3-oxo-1-butenylmercaptoacetaldehyde is accomplished by treatment thereof with base, such as an alkali metal hydroxide, methoxide or carbonate, or a secondary amine such as piperidine or diethyl amine or triethylammonium acetate; sodium or potassium methoxide, or enamine catalysis according to the procedure described in regard to Route A to produce 3-methyldihydrothiophene-2-carboxaldehyde (V).

The dialkylacetals of 2-mercaptoacetaldehyde (I), the starting materials for each of Routes A–D above, are prepared by the following improved reaction sequence.

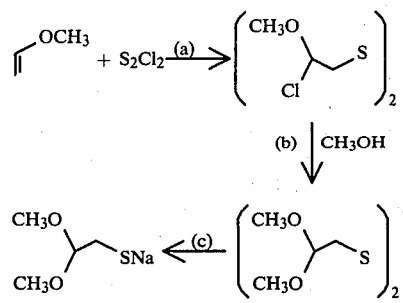

For illustration only, the dimethyl acetal derivative is used. Replacement of methyl vinyl ether by a $(C_{2-4})$alkyl vinyl ether $(R_1OCH=CH_2)$ and/or methanol by a $(C_{2-4})$alkanol or by a $(C_{2-3})$alkylene glycol affords dialkylacetals of formula I in which $R_1$ and $R_2$ when taken individually are alike or different, and when taken together are $(C_{2-3})$alkylene.

This sequence allows the use of a "one-pot" process, thus avoiding the need to isolate the endproducts of the several steps before proceeding to the next step. It affords efficient and more economical production of dialkyl acetals of formula (I) and, in particular, of 2-mercaptoacetaldehyde dimethyl acetal, derivatives of formula (X) as is described below.

The dialkylacetal products of step (c) are of sufficient purity to be used directly without isolation in further syntheses. This in situ generation of said dialkylacetal products avoids odor problems generally associated with use of said products and loss of product attendant with isolation of said product.

As demonstrated herein, the dialkylacetals of formula (I) are, especially when generated in situ, of great value as starting materials for various derivatives thereof such as those having the formula (X)

wherein $R_1$ and $R_2$ when taken individually are $(C_{1-4})$-alkyl or $R_1$ and $R_2$ when taken together are $(C_{2-3})$-alkylene as previously defined and R is $CF_3CH_2$-, $C_6H_5CH_2$— or $CH_2=CH-CH_2$—. Said compounds of formula (X) are valuable intermediates for preparation of certain well known 3-(R-substituted)-6-chloro-7-sulfamyl-3,4-dihydro-1,2,4-benzothiadiazine 1,1-dioxides useful as diuretics.

In step (a) of the above-reaction sequence, methyl vinyl ether and sulfur chloride are reacted together neat or in a reaction-inert solvent, such as carbon tetrachloride or methylene chloride at a temperature of from about $-40°$ to $+10°$ C. When the reaction is carried out neat; i.e., in the absence of a reaction-inert solvent, the methyl vinyl ether, normally a gas, is condensed to a liquid and the reaction run at from about $-40°$ C. to $-20°$ C. When a reaction-inert solvent is used the temperature range favored is from about $-10°$ to $+10°$ C. Suitable solvents in addition to carbon tetrachloride are chloroform, methylene chloride, diethyl ether, carbon disulfide, dioxane tetrahydrofuran and benzene.

The methyl vinyl ether and sulfur chloride are reacted in molar proportions of from about 2:1 to about 3:1. Reaction periods of from about one to about four hours are required depending, of course, upon the temperature.

When the reaction is run neat, the product is recovered, if desired, by allowing the temperature to rise to 10° C. to remove unreacted methyl vinyl ether. When a reaction-inert solvent is used, the solvent is removed under reduced pressure. In each instance bis(2-chloromethoxyethyl)disulfide is obtained. Said disulfide is then reacted with methanol, or other alkanol, in the presence of a base, e.g. sodium methoxide, or sodium alkoxide or sodium carbonate to produce the appropriate 1,1,1',1'-tetraalkoxy ethyl disulfide [bis(2,2-dialkoxy ethyl)disulfide].

The thioacetaldehyde dialkyl acetal disulfide [product of step (b)] is then reduced by means of sodium borohydride to provide the corresponding 2-mercaptoacetaldehyde dialkyl acetal as its sodium salt. The reduction is conveniently carried out at ambient temperature in methanol or other alkanol, preferably an alkanol, the alkyl group of which corresponds to an alkyl group of the acetal moiety. Higher of lower temperatures, e.g. from about 10° C. to 50° C. can be used but offer no advantage.

Alternatively, the reduction is readily accomplished by use of alkali metal/ammonia, e.g. sodium/ammonia at about −40° to −20° C. Evaporation of the ammonia affords the sodium salt of the 2-mercapto acetaldehyde dialkyl acetal.

The sodium salts produced in the above-described reductions can be converted to the mercaptans by neutralization with an inorganic or organic acid, if desired. However, for many purposes as described herein, the sodium salt is the desired reactant. For practical reasons the reaction mixture containing said sodium salt can be used directly. This in situ formation of the sodium salt gives rise to a "one-pot" process of value as regards the alkylation reactions to form products of formula (X) and the initial reactions of processes of Routes A-D described above.

In the reactions described herein, the sodium salts can be replaced by corresponding potassium salts, said potassium salts being formed by substitution of potassium, potassium hydroxide or other potassium salt, for the corresponding sodium salt in said reactions.

The reduction can also be carried out electrolytically. An efficient procedure comprises electrolysis in methanol—0.5M sodium acetate buffer in a Parr model 373 potentiostat (available from Parr Instrument Co.) using a carbon reference electrode and a platinum electrode as counter electrode. The disulfide is placed in the center chamber of the potentiostat and equal volumes of methanol—0.5M sodium acetate buffer placed in each chamber thereof. A 2.5 volt potential is applied and the electrolysis stopped when the current flow drops to zero. The reduced product is recovered, if desired, by combining the solutions from all chambers and evaporating to dryness. From a practical standpoint, however, it is convenient to convert the reduction product to 3-oxobutylmercaptoacetaldehyde dimethyl acetal by adjusting the pH of the combined solutions to 7.0, adding methyl vinyl ketone (from 1 to 3 moles/mole of reduction product), and concentrating the mixture to about half volume. Sodium chloride is added to the concentrate and the desired product extracted with ethyl acetate, the extract dried and evaporated to provide the 3-oxobutyl derivative.

The dialkyl acetal of 2-mercaptoacetaldehyde produced as described above can be alkylated with a compound of formula R-Z, wherein R is as previously defined, and Z is a leaving group, such as a halogen atom, especially iodo or chloro; or an alkylsulfonyloxy (e.g. mesyloxy), an arylsulfonyloxy (e.g. tosyloxy). The alkylation is carried out in a reaction-inert solvent, such as a ($C_{1-4}$) alkanol, water, dimethylacetamide or mixtures thereof at temperatures from about 0° C. to 65° C. Methanol and methanol containing mixtures, such as methanol, water, methanol-dimethylacetamide, are favored solvent systems because of the use of methanol in the process of step (c).

When mercaptoacetaldehyde dimer is used as reactant, the reaction is conducted in a reaction-inert solvent such as water, a ($C_{1-4}$)alcohol, methylene chloride, or mixtures thereof. In general, the mole ratio of dimer to methyl vinyl ketone or alpha- or beta-oxidized derivative thereof, varies from about 1:2 to 1:1. A base is sometimes used as catalyst to expedite formation of the thio anion. However, the use of a base is not necessary and the reaction, as illustrated herein, proceeds satisfactorily in the absence of a base. Representative of the bases which can be used, if desired, are tertiary amines such as pyridine, triethylamine and morpholine. Reaction temperatures range from about −20° C. to the reflux temperature of the solvent used. Reaction times, of course, depend upon the temperature and range from about 5 hours at the lower temperatures to one hour or less at the upper temperature range. The reaction mixture of the intermediate formylmethyl thio derivative is then acidified with a mineral acid and heated from 50° to reflux to achieve cyclization to the desired thiophene derivative.

The several processes described herein and the valuable and novel intermediates of said processes are exemplified in the following Examples. All temperatures are in °C.

EXAMPLE 1

1,1,1',1'-Tetramethoxyethyl Disulfide

Method A

To a stirred solution of 20.0 g. (0.33 mol) of $S_2Cl_2$ in 25 ml. of $CCl_4$ at 0° (ice-water bath) was added 20.0 g. (0.33 mol) of gaseous methyl vinyl ether at such a rate as to keep the temperature below 5°. On completion of the addition, the reaction was stripped to an oil comprising 38 g. (100%) of the bis(2-chloro-2-methoxyethyl)disulfide: $^1$H-NMR ($CDCl_3$) delta 3.20 (d, 2, J=5.8 Hz), 3.37 (s, 6H), 5.56 (t, 1, J=5.84 Hz). To the oil was added 50 ml. of methanol followed by 20.0 g. (0.37 mol) of sodium methoxide in 50 ml. of methanol keeping the reaction temperature <30° with cooling (ice bath). The reaction mixture was stripped to an oil, 100 ml. of ether added, the ether washed with 100 ml. of water, dried over $MgSO_4$, the drying agent removed by filtration and solvent removed in vacuo to afford 32.0 g. (88%) of the title product, shown to be homogeneous by glpc analysis. $^1$H-NMR ($CDCl_3$) delta 2.82 (d, 2, J=5.0 Hz), 3.25 (s, 6), 4.46 (t, 1, J=5.0 Hz). It was identical in spectral and physical characteristics to authentic material made by the process of Japanese Pat. No. 5328, 1955.

Method B

In a 3-necked round bottom flask equipped with reflux condenser, mechanical stirrer, nitrogen system and a dry ice-acetone cooling bath was condensed 200 ml. (2.68 mol) of methyl vinyl ether. The ether was stirred vigorously and kept at −40° while 93.4 ml. (1.16 mol) of $S_2Cl_2$ was added over a 30 minute period. The reaction mixture was allowed to warm to −10° and was transferred to another similarly equipped flask containing a stirred slurry of 246 g. (2.32 mol) of $Na_2CO_3$ in 500 ml. of methanol at a rate to keep the reaction temperature of the second flask <25°. The reaction was stirred 3 hours at 25°, 300 ml. of $CH_2Cl_2$ added and the salts removed from the reaction by filtration. Stripping the solvent in vacuo afforded 236 g. (84%) of the oil disulfide product: Mol dist. 120° (0.4 mm Hg); $^1$H-NMR ($CDCl_3$) delta 290 (d, 2, J=5.4 Hz), 3.29 (s, 6), 4.54 (t, 1, J=5.4 Hz).

EXAMPLE 2

1,1,1′,1′-Tetra-n-butoxyethyl Disulfide

To a 25 ml. round-bottom flask previously charged with 5.0 g. (50 mmol) of n-butyl vinyl ether and cooled to 0° was added dropwise, 3.36 g. (25 mmol) of $S_2Cl_2$ over a 30 minute period. On completion of the addition, 10.0 ml. of n-butanol was added and the solution stirred overnight at 25°, whereupon the reaction was quenched by the addition of excess saturated $NaHCO_3$ solution and ether. The ether layer was washed with water, dried over $MgSO_4$, filtered and stripped in vacuo to afford 7.6 g. (73%) of product: $^1$H-NMR ($CDCl_3$), delta 0.91 (t, 6), 2.40 (m, 8), 2.92 (d, 2H), 3.45 (m, 4), 4.41 (t, 1).

EXAMPLE 3

2,2,2-Trifluoroethylmercaptoacetaldehyde Dimethylacetal

Method A

In a 0.5 l. 3-necked round-bottom flask equipped with dry ice condenser, mechanical stirrer and under a nitrogen atmosphere was condensed 100 ml. of dry ammonia. To the rapidly stirring solution at −35° was added 9.7 g. (40 mmol) of 1,1,1′,1′-tetramethoxyethyl disulfide followed by 2.0 g. (88 mol) of sodium metal chunks. To the resulting blue reaction mixture was added, dropwise, 0.6 g. (2.5 mmol) of disulfide until the blue color disappeared and was replaced by a light yellow. The ammonia was allowed to evaporate affording a light tan solid residue shown by $^1$H-NMR to be the sodium salt of mercaptoacetaldehyde dimethylactal: $^1$H-NMR ($D_2O$), delta 2.50 (d, 2, J=5.8), 3.21 (s, 6), 4.20 (t, 1, J=5.8 Hz). To the cooled (0°) solid was added 50 ml. of cold (0°) methanol followed by 20.6 g. (8 mmol) of 2,2,2-trifluoroethyliodide and the reaction mixture heated at 60° for 2½ hours whereupon it was poured into 100 ml. of water, extracted with ethyl ether (3×75 ml.), the combined extract dried over $MgSO_4$ and the drying agent removed by filtration. Removal of solvent in vacuo afforded 15.1 g. (87%) of an oil which was vacuum distilled to afford 12.2 g. (70%) of a water white oil: B.p. 54°-5° (10 mm Hg), $^1$H-NMR ($CDCl_3$) delta 3.78 (d, 2, J=5.0 Hz), 3.18 (q, 2, J=10 Hz), 3.32 (s, 6), 4.46 (t, 1, J=5.0 Hz); $^{13}$C-NMR ($CDCl_3$) delta 125.8 (quartet, $J_{cf}$=10.9 ppm), 104.8 (d), 53.5 (q), 34.5 (t), 34.1 (quartet, $J_{ccf}$=1.29 ppm).

Method B

A solution of 50.0 g. (0.21 mol) of 1,1,1′,1′-tetramethoxyethyl disulfide 1, 4.2 g. (0.11 mol) of sodium borohydride, and 16.9 g. (0.41 mol) of sodium hydroxide in 500 ml. of 1:1 methanol/water was heated to reflux for 3 hours, cooled to 25°, 126.0 g. (0.6 mol) of 2,2,2-trifluoroethyliodide added and the reaction refluxed overnight. An additional 250 ml. of water was added and the reaction was extracted with hexane (3×250 ml.). The organic layers were dried over $Na_2SO_4$, filtered and stripped to 75 g. of a light oil which was vacuum distilled (b.p. 58°-60°, 12 mm Hg) to give 56.5 g. (67% based on disulfide reactant). It is identical to the product of Example 3, Method A.

EXAMPLE 4

2-Benzylmercaptoacetaldehyde Dimethylacetal

To a suspension of 9.7 g. (40 mmol) of 1,1,1′,1′-tetramethoxyethyl disulfide, in 30 ml. of water was added 5.33 ml. (80 mmol) of stabilized water solution of sodium borohydride (4.4 m $NaBH_4$ in 15 m NaOH, Ventron Chemical Co.). The suspension was heated under nitrogen 2 hours at 100°, cooled to 50° and, to the thus-produced sodium salt of 2-mercaptoacetaldehyde dimethylacetal, 30 ml. of methanol followed by 10.13 g. (80 mmol) of benzyl chloride were added. The reaction was stirred 5 minutes, poured into 100 ml. of water and extracted with ether (2×75 ml.). The organic layer was dried with $MgSO_4$, the drying agent removed by filtration and solvent removed in vacuo to afford 14.2 g. (84%) of benzylmercaptoacetaldehyde dimethylacetal: B.P. 114°-115° (0.5 mm Hz); $^1$H-NMR ($CDCl_3$) delta 2.51 (d, J=5.4 Hz), 3.28 (s, 6), 3.68 (s, 2), 4.33 (c, 1, J=5.4 Hz), 7.26 (s, 5); mass spectrum (70 eV), m/e 180.0604 (p—HOMe, calcd. for $C_{10}H_{12}OS$; 180.0656), 123.0303 (p—$CH_2CH(OCH_3)_2$), calcd. for $C_7H_7S$; 123.0266, 75.0352 (base, calcd. for $C_3H_7O_2$; 75.0266).

EXAMPLE 5

2-Allylmercaptoacetaldehyde Dimethylacetal

The sodium salt of 2-mercaptoacetaldehyde dimethylacetal was prepared as described in Example 4, but on 80 mmol scale, and alkylated with 6.12 g. (80 mmol) of allyl chloride affording after workup according to Example 5, 10.5 g. (82%) of allylmercaptoacetaldehyde dimethylacetal. B.p. 45°-46° (1.0 mm Hz); $^1$H-NMR ($CDCl_3$) delta 2.57 (d, 2, J=5.6 Hz), 3.15 (d, 2, J=6.8 Hz), 3.33 (5, 6), 4.42 (t, 1, J=5.6 Hz), 4.85–5.87 (m, 3, vinyl abc); mass spectrum (70 eV) m/e 130 (p—$CH_3OH$), 147 (p—$CH_3$—), 75 (base, $H_3CO=CH—OCH_3$), 73 ($CH_2=CH—CH=S^+H$).

EXAMPLE 6

1,1,1′,1′-Tetramethoxyethyl Disulfide

In a 3-necked round-bottom flask equipped with reflux condenser, mechanical stirrer, nitrogen system and placed in a dry ice-acetone cooling bath was condensed 200 ml. (2.68 mol) of methyl vinyl ether. The ether was stirred vigorously and kept at −40° to −°° while 93.4 ml. (1.16 mol) of $S_2Cl_2$ was added over a 30 minute period. The reaction mixture was allowed to warm to −10° and was transferred to another similarly equipped flask containing a stirred slurry of 246 g. (2.32 mol) of $Na_2CO_3$ in 500 ml. of methanol at a rate to keep the reaction temperature of the second flask<25°. The reaction was stirred 3 hours at 25°, 300 ml. of $CH_2Cl_2$ added and the salts removed from the reaction by filtration. Stripping of the solvent in vacuo afforded 236 g. (84%) of the oily disulfide product. Molecular distillation 120° (0.4 mm Hg); $^1$H-NMR ($CDCl_3$) delta 2.90 (d, 2, J=5.4 Hz), 3.29 (s, 6), 4.54 (t, 1, J=5.4 Hz).

EXAMPLE 7

Bis[2-(1,3-Dioxolanyl)]methyl disulfide

To 5.0 g. (17.9 mmol) of bis(2-chloro-2-methoxyethyl disulfide was added 10.0 g. (161 mmol) of ethylene glycol. The reaction was stirred 3 hours whereupon 25 ml. of chloroform was added and the organic layer washed with 50 ml. of saturated aqueous sodium bicarbonate. The organic layer was dried over $Na_2SO_4$ filtered and stripped to an oil comprising 4.3 g. (91%) which was homogeneous by TLC analysis: $^1$H-NMR ($CDCl_3$) delta 2.97 (d, 2, J=5.4 Hz), 3.91 (m, 4), 5.12 (t, 1, J=5.4 Hz); IR (film) $cm^{-1}$ 2969 (s), 2881 (s), 1474 (m), 1404 (s), 1135 (s), 1036 (s), 973 (s); mass spectrum (70 eV) m/e 238.0297 (parent, calcd. for $C_8H_{14}O_4S_2$: 238.0552).

EXAMPLE 8

3-Oxobutylmercaptoacetaldehyde dimethylacetal

Method A

To a stirred solution of 75.0 g. (0.61 mol) 2-mercaptoacetaldehyde dimethylacetal in 200 ml. of water and under a nitrogen atmosphere was added 0.5 g. of anhydrous $K_2CO_3$ followed by the dropwise addition of 50.0 g. (0.71 mol) of methyl vinyl ketone. The reaction was stirred 3 hours at ambient temperature whereupon 150 g. of NaCl was added and the solution extracted with ethyl acetate (3×200 ml.). The organic layer was dried over anhydrous $MgSO_4$ and stirred to an oil comprising 115 g. (98%), homogeneous by thin layer chromatography and nmr analysis ($SiO_2$, ether-hexane, 1:1): B.p. 90°–91° (0.45 mm Hg); $^1$H-NMR ($CDCl_3$) 2.17 (s, 3): 2.70 (cm, 6), 3.33 (s, 6), 4.45 (t, 1); ir (film) $cm^{-1}$ 1707 (s), mass spectrum (70 eV) m/e 192.0873 (calcd. for $C_8H_{16}O_3S$; 192.0968).

Anal. Calcd. for $C_8H_{16}O_3S$: C, 49.97; H, 8.38. Found: C, 49.91; H, 8.11.

Method B

A stirred solution of 0.97 g. (4.0 mmol) of 1,1,1′,1′-tetramethoxyethyl disulfide, 0.32 g. (8 mmol) of sodium hydroxide and 0.08 g. (2.0 mmol) of sodium borohydride in a solution of 8 ml. of methanol and 8 ml. of water was heated at 75° under a nitrogen atmosphere for 2 hours, cooled to 25° and 1.0 g. (12 mmol) of sodium bicarbonate and 0.97 ml. (12.0 mmol) of methyl vinyl ketone were added sequentially. The reaction was stirred 15 minutes and worked up according to the procedure of Method A above to afford 1.50 g. (98%) of keto-acetal shown to be 91% pure by glpc analysis (5′×⅛″ OV-210 on Chrom.HP at 140°) and identical to the material described above (Method A).

Method C

A solution of 9.7 g. (40 mmol) of thioacetaldehyde disulfide, 1, 8.66 g. (80 mmol) of formamidine sulfinic acid and 9.92 g. (80 mmol) of $Na_2CO_3$ in 150 ml. of water was heated for 3 hours at 65° under a nitrogen atmosphere, cooled to 25° and 8.4 g. (120 mmol) of methyl vinyl ketone added in one portion. After 5 minutes, 50 g. of NaCl was added, the reaction extracted with ether (3×100 ml.) and the ether layer dried over $MgSO_4$. Filtration and removal of solvent in vacuo afforded 13.2 g. (86%) of product as a water white oil.

Method D

A divided electrochemical cell equipped with reference electrode, mercury cathode and Pt° anode was charged with 0.5M sodium acetate buffer, and 0.485 g. (2.0 mmol) of thioacetaldehyde dimethylacetal disulfide in 26 ml. of methanol added to the chamber containing the mercury cathode. The solution was agitated with a nitrogen bubbler while a potential of 2.5 V was placed across the cell using a Parr (TM) Model 373 potentiostat until current flow had dropped to zero (2 hours), whereupon the contents of the cell were adjusted to pH 7 with acetic acid and 0.400 (5.7 mmol) of methyl vinyl ketone was added. Workup according to the procedure of Method C afforded 0.760 g. (100%) of an oil shown by $^1$H-NMR analysis to be the title product.

EXAMPLE 9

3-Methyl-4,5-Dihydrothiophene-2-Carboxaldehyde

A solution of 20.0 g. (0.104 mol) of (3-oxobutyl)-mercaptoacetaldehyde dimethylacetal in 100 ml. of 1.0N HCl was clarified by the addition of 20 ml. of acetone and allowed to stir for 15 minutes whereupon 25 g. of NaCl was added and the aqueous solution of keto-aldehyde was extracted into ethyl acetate (3×100 ml.). The ethyl acetate was dried over $MgSO_4$, filtered, and stripped to 15.0 g. (100%) of (3-oxobutyl)mercaptoacetaldehyde: $^1$H-NMR ($CDCl_3$) delta 2.14 (s, 3), 2.70 (m, 4), 3.23 (d, 2, J=3.4 Hz), 9.51 (t, 1, J=3.4 Hz); IR (film) $cm^{-1}$ 1710 (s). The keto aldehyde was placed in 50 ml. of $CHCl_3$ with 5.0 g. of $MgSO_4$ and a mixture of 0.17 ml. (2.0 mmol) of pyrrolidine in 0.21 ml. (3.5 mmol) of acetic acid was added. The reaction was stirred 2 hours at ambient temperature until a single new product was observed by $^1$H-NMR. The reaction was filtered, the $CHCl_3$ washed with 1N HCl (50 ml.), water (50 ml.), saturated $NaHCO_3$ (50 ml.) and dried over anhydrous $MgSO_4$. Filtration and removal of solvent in vacuo afforded 10.2 g. (80%) of an oil, homogeneous by TLC ($SiO_2$, ethyl acetate/hexane, 3:2). Attempted distillation afforded a mixture of 3-methyl-4,5-dihydrothiophene-2-carboxaldehyde, 3-methylthiophene-2-carboxaldehyde, and the fully saturated 3-methyl-2,3,4,5-tetrahydrothiophene-2-carboxaldehyde as a mixture of epimers. Chromatography on silica gel using ether/hexane, 1:1 as eluent afforded a sample of the title product for analysis: M.p. 33.5°–34°, $^1$H-NMR ($CDCl_3$) delta 2.20 (s, 3), 3.13 (m, 4), 10.0 (s, 1H); IR (KBr) $cm^{-1}$ 1662 (s), 1607 (s); mass spectrum (70 eV) m/e 128.0304 (parent and base, calcd. for $C_6H_8OS$; 128.0354), 99.0288 (p—CHO, calcd. for $C_5H_7S$; 99.0276), 83.0077 ($C_4H_3S$).

Repetition of this procedure but using morpholine or piperidine in place of pyrrolidine affords similar results.

EXAMPLE 10

3-Methyl-4,5-Dihydrothiophene-2-Carboxaldehyde

A solution of 35.0 g. (182 mmol) of (3-oxobutyl)-mercaptoacetaldehyde dimethylacetal in 350 ml. of 0.5N $H_2SO_4$ and 20 ml. of acetone was stirred at ambient temperature for 30 minutes followed by the removal of acetone at low pressure (100 mm Hg) for 18 minutes. After the addition of 50 g. of NaCl, the solution was extracted with $CHCl_3$ (4×100 ml.), the $CHCl_3$ layer dried over $MgSO_4$ and the drying agent removed by filtration. The dried $CHCl_3$ solution of (3-oxobutyl)-mercaptoacetaldehyde was allowed to percolate through a 15×150 mm column of IRA-45 (TM Rohm &

Haas) ion exchange resin (acetate form) at a flow rate of 2 ml./minute. NMR indicated the effluent containing 3-methyl-4,5-dihydrothiophene-2-carboxaldehyde >95% pure. The column was washed with some CHCl$_3$ and the combined effluent concentrated in vacuo to 19.9 g. of crude oil (86%) show by NMR analysis to be 71% pure 3-methyl-4,5-dihydrothiophene-2-carboxaldehyde (67% overall yield from ketoacetal reactant).

EXAMPLE 11

3-Methyl-2-Thiophenecarboxaldehyde

Method A

A slurry of 1.28 g. (10 mmol) of 3-methyl-4,5-dihydrothiophene-2-carboxaldehyde, and 3.70 g. (15 mmol) of o-chloranil in 10 ml. of dioxane was refluxed 3 hours until starting material had been consumed (as evidenced by TLC analysis on SiO$_2$ using ethyl acetate/hexane 1:2 as eluent). On cooling, the reaction mixture was filtered through silica gel, the silica gel washed with CHCl$_3$ and the CHCl$_3$ removed in vacuo to afford 0.90 g. (72%) of 3-methyl-2-thiophenecarboxaldehyde.

Method B

To a stirred suspension of 67 g. (0.77 mol) of activated MnO$_2$ in benzene under a nitrogen atmosphere was added 20.0 g. (0.156 mol) of 3-methyl-4,5-dihydrothiophene-2-carboxaldehyde, in one portion. When the initial exotherm had subsided, the reaction mixture was refluxed for 3 hours whereupon an additional 20 g. (0.23 mol) of MnO$_2$ was added. After 1.5 hours of reflux the reaction mixture was cooled and the MnO$_2$ removed by filtration through a bed of diatomaceous earth. The MnO$_2$ cake was washed with 100 ml. of ether, and the combined washes stripped to an oil comprising 20.2 g. (100%). Distillation afforded 11.5 g. of 3-methyl-2-thiophene-carboxaldehyde (B.p. 94°–96°, 20 mm Hg).

The oxidation as described above was repeated on 0.602 mole scale with 3.68 mole of MnO$_2$ using toluene as solvent. The reaction was heated to 80° for 3 hours, cooled and product isolated as before affording 60.0 g. (80%) of 3-methylthiophene-2-carboxaldehyde.

The actived MnO$_2$ was prepared as follows: To a mechanically stirred solution of 50 ml. of concentrated HNO$_3$ in 200 ml. of water at 70° was added portionwise 100 g. of MnO$_2$.hydrate (Chemetals Corp. Type M). On completion of the addition, the temperature was raised to 100° and the slurry stirred for 30 minutes. After cooling, the MnO$_2$ was isolated by filtration, washed with 1.5 l. of H$_2$O, 0.5 l. of 1% NaHCO$_3$, 1.5 l. of H$_2$O, acetone (3×300 ml.) and dried in vacuo 12 hours at 50°. The dried solids comprised 81.0 g. (82%).

Method C

To a stirred solution of 128 mg. (1.0 mmol) of 3-methyl-4,5-dihydrothiophene-2-carboxaldehyde in 2 ml. of acetone was added 138 mg. (1.0 mmol) of N-bromoacetamide. After stirring 3 hours at ambient temperature, glpc assay (5'×⅛", 3% OV-210 on Chrom HP at 110° C.) of the reaction mixture relative to internal standard (p-cresol methyl ether) indicated the presence of 3-methyl-2-thiophenecarboxaldehyde in 27% yield.

Method D

To a solution of 128 mg. (1 mmol) of 3-methyl-4,5-dihydrothiophene-2-carboxaldehyde in 3 ml. of CDCl$_3$ was added 134 mg. (1 mmol) of N-chlorosuccinimide. The reaction was stirred at ambient temperature for 1.5 hours. $^1$H-NMR assay relative to diphenylmethane internal standard showed the presence of 3-methylthiophene-2-carboxaldehyde in 27% yield.

Methods E-H

Following the procedure of Method C, but using diphenyldisulfide, 2,3-dichloro-5,6-dicyanobenzoquinone, sulfur or nickel peroxide as oxidant affords 3-methyl-2-thiophenecarboxaldehyde.

EXAMPLE 12

3-Methylthiophene-2-Carboxaldehyde

A stirred suspension of 84.0 g. (0.437 mol) (3-oxobutyl)mercaptoacetaldehyde dimethylacetal, in 840 ml. of 0.5N H$_2$SO$_4$ and 40 ml. of acetone at 25° under a nitrogen atmosphere was stirred 30 minutes, placed under vacuum (~100 mm Hg) for 15 minutes and finally extracted with CHCl$_3$ (4×250 ml.). The CHCl$_3$ layer was placed in a 3-necked round bottom flask equipped with mechanical stirrer, reflux condenser and nitrogen system, and previously charged with 42 g. MgSO$_4$ and 19.6 g. (133 mmol) of morpholine acetate. The reaction was stirred 45 minutes until the formation of dihydrothiophene was complete as evidenced by $^1$H-NMR analysis and then 180 g. (2.1 mol) of activated MnO$_2$ was added, the reaction stirred at reflux for 12 hours until $^1$H-NMR analysis showed complete conversion to 3-methylthiophene-2-carboxaldehyde.

The reaction was filtered hot through diatomaceous earth and the MnO$_2$ washed with 500 ml. of hot CHCl$_3$. The combined filtrate and wash comprised 700 ml. and was shown to contain product in 69% overall yield by gplc assay (5'×⅛" 3% OV-210 at 120°). An aliquot comprising 330 ml. of the total CHCl$_3$ solution was extracted with 1N H$_2$SO$_4$ (2×250 ml.), the aqueous wash back extracted with 100 ml. of CHCl$_3$ and the combined organic layers dried over MgSO$_4$. Filtration followed by isolation in vacuo afforded an oil which was distilled [B.p. 52° (0.03 mm Hg)] to yield 15.2 g. of product of 99.2% purity as evidenced by hplc analysis (ODS-2 using H$_2$O/CH$_3$CN, 80:20 eluent at 2600 psi and 3.0 ml./minute), and identical in all respects to an authentic sample.

EXAMPLE 13

3-Methylthiophene-2-Carboxaldehyde

Methyl vinyl ether (1.15 mol) was condensed and stirred at −40° while S$_2$Cl$_2$ (0.5 mol) was slowly added over 30 minutes keeping the pot temperature below −20°. The reaction was allowed to warm to 0° and the solution then slowly added to a suspension of Na$_2$CO$_3$ (106 g., 1.0 mol) in 0.43 l. of methanol, keeping the pot temperature below 25°. The mixture was stirred 3 hours, filtered and stripped to an oil. The yield based of bis(2-chloro-2-methoxyethyl)disulfide was 100% based on S$_2$Cl$_2$.

To the crude disulfide oil (1 mol) was added 0.625 l. of water and 0.136 l. of NaBH$_4$ (stabilized water solution: 4.4M NaBH$_4$ in 15M NaOH; 0.583 mol NaBH$_4$, 1.988M NaOH). The biphasic mixture was refluxed 4–5 hours whereupon complete solution of the disulfide occurred. The reaction mixture was cooled to 25° and 102 ml. of acetic acid added (2.0 mol). The reaction (which now contains free thiol) was quenched by the rapid addition of methyl vinyl ketone (2.2 mol). After 15 minutes the reaction mixture separated into two layers. The layers were separated and the aqueous layer extracted once with CH$_2$Cl$_2$. Combination of the organic layers, drying over MgSO$_4$ and removal of solvent in vacuo afforded 3-oxobutylmercaptoacetaldehyde dimethyl acetal as an oil. The overall yield based on S$_2$Cl$_2$=85–90%.

To 1.9 l. of 0.5N H$_2$SO$_4$ and 0.190 l. of acetone was added 192 g. (mw 192, 1 mol) of dimethylacetal. The reaction mixture was stirred at ambient temperature for 30 minutes and extracted with CHCl$_3$ (3×1.33 l.). To the CHCl$_3$ extract was added 50 g. MgSO$_4$, and a mixture of 40 ml. (0.67 mol) acetic acid with 33 ml. (0.38 mol) of morpholine. The reaction was stirred 30 minutes at ambient temperature and 522 g. of activated MnO$_2$ was added. The reaction was then stirred at reflux 4–6 hours, MnO$_2$ filtered off and CHCl$_3$ removed in vacuo to afford crude 3-methylthiophene-2-carboxaldehyde contaminated with MnO$_2$ residues, acetic acid and morpholine. The overall yield based on keto-acetal was 70–88%. It was purified by washing the CHCl$_3$ solution with 1N H$_2$SO$_4$, drying over MgSO$_4$, filtration and distillation at reduced pressure (B.p. 52°, 0.03 mm Hg) affording 38.5 g. of product (~90% recovery over the purification step).

EXAMPLE 14

3-Acetoxy-3-Buten-2-one

To a solution of 19.6 g. (228 mol) of 2,3-butanedione in 200 ml. of ether was added 3.34 g. (27 mmole) of dimethylamino pyridine, and 23 g. (228 mmole) of triethylamine. The solution was cooled to 0° and 23.24 g. (228 mmol) of acetic anhydride was added dropwise with vigorous stirring. The clear yellow solution was allowed to warm to 25° and was stirred 3 hours. The reaction mixture was transferred to a separatory funnel, washed with water (3x) and dried over MgSO$_4$. Filtration and evaporation in vacuo afforded 17.6 g. of crude 3-acetoxy-3-buten-2-one (assayed by $^1$H-NMR with internal standard as 91% pure, 56% yield): $^1$H-NMR (CDCl$_3$) delta 2.06 (s, 3), 2.25 (s, 3), 5.42, 5.49, 5.79, 5.82 (AB, 2).

Repetition of this procedure but using propionic or butyric anhydrides in place of acetic anhydride affords the corresponding 3-propionyloxy- and 3-butyryloxy-3-buten-2-ones.

EXAMPLE 15

2-Acetoxy-3-Oxobutylmercaptoacetaldehyde Dimethylacetal

To a solution of 15 g. (0.123 mol) of 2-mercaptoacetaldehyde dimethylacetal in 150 ml. of methanol was added 225 mg. of K$_2$CO$_3$ and 15.8 g. (0.123 mol) of 3-acetoxy-3-buten-2-one. After 2 hours at ambient temperature, the solvent was removed in vacuo, the oily residue dissolved in ether, washed with water and dried over Na$_2$SO$_4$. Filtration and removal of solvent in vacuo afforded 24.9 g. (81%) of the crude product: $^1$H-NMR (CDCl$_3$) delta 2.15 (s, 3), 2.19 (s, 3), 2.74 (d, 2, J=5.4 Hz), 3.03 (m, 2), 3.34 (s, 6), 4.50 (t, 1, J=5.4 Hz), 5.22 (d of d, 1); $^{13}$C-NMR (CDCl$_3$) delta 203.5 (s), 169.7 (s), 104.6 (d), 77.5 (d), 53.5 (q), 53.3 (q), 34.5 (d), 32.4 (t), 26.6 (q), 20.3 (q); mass spectrum (70 eV) m/e 250.0855 (parent, calcd. for C$_{10}$H$_{18}$O$_5$S; 250.1134); IR (film) cm$^1$ 1747 (s), 1733 (s).

In like manner, 2-propionyloxy- and 3-butyryloxy-3-oxobutylmercaptoacetaldehyde dimethylacetals are prepared from 3-propionyloxy- and 3-butyryloxy-3-buten-2-one.

EXAMPLE 16

3-Methylthiophene-2-Carboxaldehyde

A solution of 250 mg. (1.0 mmol) of 2-acetoxy-3-oxobutylmercaptoacetaldehyde dimethylacetal in 0.83 ml. of 3N HCl and 2.3 ml. of isopropanol was heated at 75° under a nitrogen atmosphere for 8 hours. Glpc analysis (⅛"×5' 3% OV-210 on Chrom. HP, 60–80 mesh at 130°) showed the presence of 3-methylthiophene-2-carboxaldehyde in 79% yield. Extraction of the reaction mixture with ethyl ether afforded 168 mg. of product identical in $^1$H-NMR, TLC (silica gel, ethyl acetate/hexane, 1:4) and glpc analysis to an authentic sample thereof.

Similarly, the remaining compounds of Example 15 are converted to the title product.

EXAMPLE 17

3-Oxo-2-Hydroxybutylmercaptoacetaldehyde Dimethylacetal

To a solution of 200 mg. (0.8 mmol) of 2-acetoxy-3-oxobutylmercaptoacetaldehyde dimethylacetal in 2 ml. of methanol was added 110 mg. (0.8 mmol) of K$_2$CO$_3$. The reaction mixture was stirred 10 minutes, filtered, diluted with water and extracted with CHCl$_3$. The CHCl$_3$ extract was dried over Na$_2$SO$_4$, filtered and evaporated to 123 mg. (75%) of keto alcohol product: $^1$H-NMR (CDCl$_3$) delta 2.20 (s, 3), 2.85 (m, 4), 3.32 (s, 6), 4.32 (m, 1), 4.45 (t, 1).

EXAMPLE 18

3-Methylthiophene-2-Carboxaldehyde

A solution of 210 mg. (1.0 mmol) of 3-oxo-2-hydroxybutylmercaptoacetaldehyde dimethylacetal in 2 ml. of 1N HCl and 0.5 ml. of isopropanol was heated to 75° and stirred for 4.5 hours under a nitrogen atmosphere. On cooling, 8 ml. of water was added, the reaction extracted with ether, and the ether dried over Na$_2$SO$_4$. A yield for 3-methylthiophene-2-carboxaldehyde of 24% was determined by the addition of internal standard and glpc analysis ⅛"×5' 3% OV-210, Chrom HP, 60–80 mesh at 130°, and flow rate of 3.5 ml./min.).

EXAMPLE 19

(3-Oxo-1-butenyl)mercaptoacetaldehyde Dimethylacetal

Method A

To a stirred solution of 17.9 g. (0.147 mol) 2-mercaptoacetaldehyde dimethylacetal and 100 mg. of K$_2$CO$_3$ in 80 ml. of methanol under a nitrogen atmosphere and cooled to −30° was added dropwise a solution of 10.0 g. (0.147 mol) of 3-butyne-2-one, in 20 ml. of methanol. The reaction was highly exothermic until half of the addition of 3-butyne-2-one was completed. The reaction was allowed to stir one hour at −30°, warmed to ambient temperature and stripped to an oil under vacuum. The resulting oil was placed in 100 ml. of ether, washed successively with water (3×50 ml.) and brine (50 ml.) and dried over MgSO$_4$. Filtration followed by removal of solvent in vacuo afforded 21.2 g. (76%) of a yellow oil shown to be an 85:15 mixture of Z and E isomers by $^1$H-NMR: Mol dist 165° (0.2 mm Hg); $^1$H-NMR (CCl$_4$) delta 2.09 (s, 3), 2.74 (d, 2, J=5.4 Hz), 3.26 (s, 3), 3.31 (s, 3), 4.39 (t, 1, J=5.4 Hz), 6.17 (d, 1, J=9.8 Hz), 7.06 (d, 1, J=9.8 Hz); IR (film) cm$^{-1}$ 1661 (s), 726 (m); mass spectrum (70 eV) m/e 190.0653 (calcd. for C$_8$H$_{14}$O$_3$S; 190.0812), $^{13}$C-NMR (CDCl$_3$) 196.1 (s), 149.6 (d), 112.0 (d), 104.5 (d), 53.9 (q), 38.7 (t), 29.6 (q).

The minor isomer exhibited the following spectral characteristics: $^1$H-NMR (CCl$_4$) delta 2.09 (s, 3), 2.94 (d, J=5.4 Hz), 3.26 and 3.31 (s, 6), 4.44 (t, 1, J=5.4 Hz), 5.97 (d, 1, J=16 Hz), 7.47 (d, 1, J=16 Hz); IR (film) cm$^{-1}$ 1661 (s), 973 (s): $^{13}$C-NMR (CDCl$_3$) delta 193.9, 146.3, 123.7, 102.7, 53.8, 34.6, 27.2.

Method B

To a stirred solution of 1.0 g. of 1-methoxy-3-oxobutylmercaptoacetaldehyde dimethylacetal in 100 ml. of dry methanol was added 1.0 g. anhydrous K$_2$CO$_3$. The slurry was heated at reflux for 3 hours whereupon the methanol was removed in vacuo and the residue taken up in ether. The ether solution was washed with water, then dried over anhydrous granular Na$_2$SO$_4$. Removal of the solvent under reduced pressure afforded 0.54 g. of a clear oil shown by $^1$H-NMR to be an 80:20 mixture of Z and E isomers and identical in spectral characteristics to the product of Method A.

A solution of 1.0 g. (15.7 mmol) of 1-methoxy-3-oxobutylmercaptoacetaldehyde dimethylacetal in 30 ml. of 0.1N HCl was heated at 65° and followed by TLC analysis (SiO$_2$, ethyl ether eluent). Initial hydrolysis of the acetal to 1-methoxy-3-oxobutylmercaptoacetaldehyde was followed by the sequential appearance of (3-oxo-1-butenyl)thioacetaldehyde and 3-methylthiophene-2-carboxaldehyde.

EXAMPLE 20

(3-Oxo-1-butenyl)mercaptoacetaldehyde

A solution of 3.0 g. (15.7 mmol) of (3-oxo-1-butenyl)-mercaptoacetaldehyde dimethylacetal in 30 ml. of 10:1 trifluoroacetic acid/water at 0° was stirred 2 hours, poured into 150 ml. of water and extracted with CHCl$_3$ (4×50 ml.). The CHCl$_3$ was washed with cold aqueous saturated NaHCO$_3$ solution, dried over Na$_2$SO$_4$, filtered and stripped in vacuo to afford 2.1 g. (93%) of the crude mixture of aldeyde double bond isomers (68:32::E to Z). Column chromatography on silica gel using ethyl ether as eluent afforded both isomers in a ratio of 4:1::E:Z. The (Z-3-oxo-1-butenyl)mercaptoacetaldehyde eluted first: R$_f$0.45, $^1$H-NMR (CDCl$_3$) delta 2.25 (s, 3), 3.45 (d, 2, J=3.2 Hz), 6.38 (d, 1, J=9.8 Hz), 6.80 (d, 1, J=9.8 Hz), 9.62 (t, 1, J=3.2 Hz); IR (KBr) cm$^{-1}$ 1721 (m), 1659 (s); mass spectrum (70 eV) m/e 144.0240 (parent, calcd. for C$_6$H$_8$O$_2$S; 144.0354), 126.0130 (p—H$_2$O, calcd. for C$_6$H$_6$OS; 126.0198), 115.0230 (p—CHO), 97 (p—CHO and —OH$_2$). The Eolefin isomer (R$_f$ 0.3) exhibited the following spectral characteristics: $^1$H-NMR (CDCl$_3$) delta 1.94 (s, 3), 3.38 (d, 2, J=3.2 Hz), 5.85 (d, 1, J=15.9 Hz), 7.24 (d, 1, J=15.9 Hz), 9.35 (t, 1, J=3.2 Hz); IR (film) cm$^{-1}$ 1724 (m), 1660 (s); mass spectrum (70 eV) m/e 144.0242 (parent, calcd. for C$_6$H$_8$O$_2$S: 144.0354), 101.0053 (base, p—CH$_2$CHO, calcd. for C$_4$H$_5$Os; 101.0120).

EXAMPLE 21A–E

3-Methylthiophene-2-Carboxaldehyde

The following conditions afforded the indicated yields of title product from EZ-3-oxo-1-butenylmercaptoacetaldehyde based on glpc analysis (5'×⅛"3% OV-210 on Chrom HP at 120°) relative to internal standard.

Method A. Aldehyde in methanol with 1 equivalent of K$_2$CO$_3$ for 25 minutes at ambient temperature (17%).

Method B. Aldehyde in benzene with 10 mol % pyrrolidine acetate catalyst at reflux for 75 minutes (15%).

Method C. Aldehyde in methanol at 25° with 1 equivalent of sodium methoxide for 20 minutes (20%).

Method D. Aldehyde in benzene with 1 equivalent of triethylammonium acetate at reflux for 20 minutes (14%).

Method E. Aldehyde in benzene with 2 equivalents of methyl formate, and 1 equivalent of diethylamine at 25° for 1 hour (14%).

EXAMPLE 22

1-Methoxy-3-oxo-butylmercaptoacetaldehyde Dimethyl Acetal

To a solution of 2.3 g. (18.9 mmol) of 4-methoxy-3-buten-2-one and 50 mg. K$_2$CO$_3$ in 15 ml. of methanol was added 1.88 g. (18.9 mmol) of 2-mercaptoacetaldehyde dimethyl acetal and the reaction mixture heated to reflux for 10 minutes. On cooling, the methanol was removed by rotatory evaporation, 25 ml. of ether was added and the solution was extracted with water, brine, and dried over anhydrous magnesium sulfate. Filtration and removal of solvent afforded 2.95 g. (70%) of water white oil homogeneous by TLC (SiO$_2$), tetrahydrofuran/ether, 1:1; Mol. dist. 140° (0.2 mm Hg), $^1$H-NMR (CDCl$_3$) delta 2.21 (s, 3), 2.66–3.11 (m, 4), 3.42 (s, 9), 4.44 (t, 1), 4.89 (doublet of doublets, 1); IR (film) cm$^{-1}$ 1710 (s).

EXAMPLE 23

3-Methylthiophene-2-Carboxaldehyde

A solution of 0.5 g. (2.25 mmol) of 1-methoxy-3-oxobutylthioacetaldehyde dimethyl acetal in 5.0 ml. of 0.5N HCl was heated 18 hours at 50° and after cooling extracted with 10 ml. of ether. The ether layer was dried (MgSO$_4$), filtered and evaporated in vacuo to afford 0.34 g. of an oil shown by glpc analysis (5', 3% OV-1 on Chrom HP at 175°) to consist of a 60:40 mixture of 3-methylthiophene-2-carboxaldehyde and 3-acetylthiophene, respectively.

EXAMPLE 24

1-methoxy-3-oxobutylmercaptoacetaldehyde

A solution of 0.5 g. (2.25 mmol) of 1-methoxy-3-oxobutylmercaptoacetaldehyde dimethyl acetal, (ketoacetal reactant) in 35 ml. of 0.5N HCl and 2 ml. of acetone was stirred at ambient temperature for 24 hours. The reaction was extracted with ether, then dried (MgSO$_4$) filtered and evaporated in vacuo to afford 0.4 g. of an oil exhibiting a single —CHO triplet at 9.58 ppm: $^1$H-NMR (CDCl$_3$) delta 2.20 (s, 3), 2.90 (m), 3.40 (s), 4.78 (m), 9.58 (t).

The hydrolysis was better performed by the use of trifluoroacetic acid/water. A solution of 1.0 g. of keto acetal reactant in 10 ml. of 9:1 trifluoroacetic acid water at 0° was stirred for 2 hours. The reaction was stopped by the addition of 50 ml. of ice water, extracted with CHCl$_3$ (2×35 ml.), dried (MgSO$_4$), filtered and evaporated to 0.60 g. (76%) of an oil shown by $^1$H-NMR to contain the desired product.

EXAMPLE 25

3-Oxobutylmercaptoacetaldehyde Ethyleneacetal

To a three-necked round flask equipped with dry ice-acetone condenser, mechanical stirrer, and nitrogen inlet was condensed 60 ml. (0.80 moles) of methyl vinyl ether. The ether was stirred and kept at $-20°\pm5°$ while 20 ml. of sulfur monochloride (0.25 moles) was added dropwise over 25 minutes. The resulting clear yellow solution was warmed to 0° and then 77.0 g. of ethylene glycol (1.20 moles) was added over 10 minutes. The heterogeneous mixture was vigorously stirred, warmed to, and maintained at, 25° for 45 minutes. Volatiles were stripped from the deep purple reaction mixture at reduced pressure (5-20 mm) with heating up to 50° C. $^1$H-NMR (CCl$_4$) of the crude product showed that bis-[2-(1,3-dioxolanyl)methyl]disulfide [delta 2.85 (d, J=5.4 Hz), 3.80 (m, 4), 4.90 (t, J=5.4 Hz)] was the predominant product.

The crude disulfide was added to 313 ml. of deionized water, 72 ml. of NaBH$_4$ solution (4.4M NaBH$_4$ and 15M NaOH) was slowly added. Once initial outgassing ceased, the heterogeneous mixture was heated to reflux (100-104°) and maintained at reflux for 4 hours to give a clear yellow solution. Upon cooling to room temperature an oil precipitated and the solution darkened. When 51 ml. of glacial acetic acid (0.89 moles) was added, vigorous gas evolution occurred. Methyl vinyl ketone (77.9 g., 110 mmoles) was added to the stirred mixture. Stirring was continued for 30 minutes and then stopped to allow layer separation. The aqueous layer was extracted with CH$_2$Cl$_2$ (2×100 ml.) and then the extracts were added to the initial organic layer. The combined organic phases were dried over anhydrous MgSO$_4$, filtered, and then distilled at reduced pressure to give 66.0 g. (70% yield from S$_2$Cl$_2$) of the title product: B.p. 80°-90° at 0.03 mm. $^1$H-NMR (CDCl$_3$) delta 2.10 (s, 3), 2.60 (d, 2), 2.71 (m, 4), 3.83 (m, 4), 4.90 (t, 1).

EXAMPLE 26

3-Methylthiophene-2-Carboxaldehyde

Crude 2-acetoxy-3-oxobutylmercaptoacetaldehyde ethyleneacetal (750 mg., 3.02 mmol, prepared according to the procedure of Example 25 but using 3-acetoxy-3-buten-2-one in place of methyl vinyl ketone) was dissolved in 10 ml. of isopropanol and 3.0 ml. of 3N HCl. The solution was stirred under nitrogen while being heated for 6 hours at 70°-75° C. The black reaction mixture was cooled to room temperature and then extracted with CH$_2$Cl$_2$ (2×15 ml.). The organic layers were combined and dried over MgSO$_4$, filtered, and then concentrated at reduced pressure to an oil (575 mg.). An $^1$H-NMR of the crude oil showed 3-methylthiophene-2-carboxaldehyde to be the major product.

EXAMPLE 27

3-Methylthiophene-2-Carboxaldehyde (via 1,4-dithian-2,5-diol)

A mixture of 8.36 g. (0.055 mole) of 1,4-dithian-2,5-diol in 100 ml. water was stirred and heated to reflux. 2-Acetoxy-3-oxo-1-buten (12.8 g., 0.1 mole) was then added over a five minute period and the reaction mixture refluxed for one hour. It was then acidified by addition of 5 ml. concentrated HCl and refluxed overnight. The product was recovered by extracting the cooled reaction mixture with methylene chloride, drying the extract (MgSO$_4$) and evaporating it under reduced pressure. Yield=4.4 g. (35%) of title product.

I claim:

1. The compound having the formula

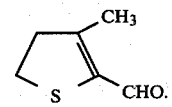

* * * * *